United States Patent
Wang et al.

(10) Patent No.: US 11,961,227 B2
(45) Date of Patent: Apr. 16, 2024

(54) METHOD AND DEVICE FOR DETECTING AND LOCATING LESION IN MEDICAL IMAGE, EQUIPMENT AND STORAGE MEDIUM

(71) Applicant: Ping An Technology (Shenzhen) Co., Ltd., Guangdong (CN)

(72) Inventors: Yue Wang, Guangdong (CN); Bin Lv, Guangdong (CN); Chuanfeng Lv, Guangdong (CN)

(73) Assignee: Ping An Technology (Shenzhen) Co., Ltd., Guangdong (CN)

( * ) Notice: Subject to any disclaimer, the term of this patent is extended or adjusted under 35 U.S.C. 154(b) by 611 days.

(21) Appl. No.: 17/168,884

(22) Filed: Feb. 5, 2021

(65) Prior Publication Data
US 2021/0166383 A1    Jun. 3, 2021

Related U.S. Application Data

(63) Continuation of application No. PCT/CN2019/117098, filed on Nov. 11, 2019.

(30) Foreign Application Priority Data
Aug. 5, 2019    (CN) .......................... 201910718497.3

(51) Int. Cl.
   *G06T 7/00*    (2017.01)
   *A61B 5/00*    (2006.01)
   (Continued)

(52) U.S. Cl.
   CPC .......... *G06T 7/0012* (2013.01); *A61B 5/0066* (2013.01); *A61B 5/4887* (2013.01);
   (Continued)

(58) Field of Classification Search
   CPC ........ G06T 7/0012; G06T 7/11; G06T 7/136; G06T 7/187; G06T 7/73;
   (Continued)

(56) References Cited

U.S. PATENT DOCUMENTS

| | | |
|---|---|---|
| 2016/0162757 A1 | 6/2016 | Chen et al. |
| 2019/0122360 A1 | 4/2019 | Zhang et al. |

FOREIGN PATENT DOCUMENTS

| | | |
|---|---|---|
| CN | 106780460 A | 5/2017 |
| CN | 107766794 A | 3/2018 |

(Continued)

OTHER PUBLICATIONS

Gondal, W.M., Köhler, J.M., Grzeszick, R., Fink, G.A. and Hirsch, M., Sep. 2017. Weakly-supervised localization of diabetic retinopathy lesions in retinal fundus images. In 2017 IEEE international conference on image processing (ICIP) (pp. 2069-2073). IEEE.*

(Continued)

*Primary Examiner* — Zhitong Chen
(74) *Attorney, Agent, or Firm* — IP Spring

(57) ABSTRACT

A method for detecting and locating a lesion in a medical image is provided. A target medical image of a lesion is obtained and input into a deep learning model to obtain a target sequence. A first feature map output from the last convolution layer in the deep learning model is extracted. A weight value of each network unit corresponding to each preset lesion type in a fully connected layer is extracted. For each preset lesion type, a fusion feature map is calculated according to the first feature map and the corresponding weight value and resampled to the size of the target medical image to generate a generic activation map. The maximum connected area in each generic activation map is determined, and a mark border surrounding the maximum connected area (Continued)

is created. A mark border corresponding to each preset lesion type is added to the target medical image.

14 Claims, 6 Drawing Sheets

(51) Int. Cl.

| | | |
|---|---|---|
| *A61B 6/03* | (2006.01) | |
| *G06F 18/21* | (2023.01) | |
| *G06F 18/214* | (2023.01) | |
| *G06F 18/2415* | (2023.01) | |
| *G06F 18/25* | (2023.01) | |
| *G06T 7/11* | (2017.01) | |
| *G06T 7/136* | (2017.01) | |
| *G06T 7/187* | (2017.01) | |
| *G06T 7/73* | (2017.01) | |
| *G06V 10/764* | (2022.01) | |
| *G06V 10/774* | (2022.01) | |
| *G06V 10/776* | (2022.01) | |
| *G06V 10/80* | (2022.01) | |
| *G06V 10/82* | (2022.01) | |

(52) U.S. Cl.
CPC .......... *A61B 5/7267* (2013.01); *A61B 5/7275* (2013.01); *A61B 6/032* (2013.01); *G06F 18/2148* (2023.01); *G06F 18/217* (2023.01); *G06F 18/2415* (2023.01); *G06F 18/253* (2023.01); *G06T 7/11* (2017.01); *G06T 7/136* (2017.01); *G06T 7/187* (2017.01); *G06T 7/73* (2017.01); *G06V 10/764* (2022.01); *G06V 10/774* (2022.01); *G06V 10/776* (2022.01); *G06V 10/806* (2022.01); *G06V 10/82* (2022.01); *G06T 2207/20081* (2013.01); *G06T 2207/30096* (2013.01); *G06V 2201/03* (2022.01)

(58) Field of Classification Search
CPC . G06T 2207/20081; G06T 2207/30096; G06T 2207/10101; G06T 2207/30041; A61B 5/0066; A61B 5/4887; A61B 5/7267; A61B 5/7275; A61B 6/032; G06F 18/2148; G06F 18/217; G06F 18/2415; G06F 18/253; G06F 18/2431; G06F 18/214; G06V 10/764; G06V 10/774; G06V 10/776; G06V 10/806; G06V 10/82; G06V 2201/03; G06V 10/25; G06N 3/045; G06N 3/08

See application file for complete search history.

(56) References Cited

FOREIGN PATENT DOCUMENTS

| | | |
|---|---|---|
| CN | 109102491 A | 12/2018 |
| CN | 109410204 A | 3/2019 |
| CN | 109685077 A | 4/2019 |
| CN | 109829446 A | 5/2019 |
| CN | 109949318 A | 6/2019 |

OTHER PUBLICATIONS

Zhou, B., Khosla, A., Lapedriza, A., Oliva, A. and Torralba, A., 2016. Learning deep features for discriminative localization. In Proceedings of the IEEE conference on computer vision and pattern recognition (pp. 2921-2929).*

CNIPA, International Search Report for International Patent Application No. PCT/US2019/117098, 4 pages, Apr. 29, 2020.

CNIPA, First Office Action for corresponding Chinese Patent Application No. CN201910718497.3, Mar. 17, 2022, 15 pages.

Gondal, Waleed M., et al., "Weakly-supervised localization of diabetic retinopathy lesions in retinal fundus images," IEEE international conference on image processing (ICIP), <<arXiv:1706.09634v1>>, Jan. 29, 2017, pp. 1-5.

* cited by examiner

CLIENT                                    SERVER

METHOD AND DEVICE FOR DETECTING AND LOCATING LESION IN MEDICAL IMAGE, EQUIPMENT AND STORAGE MEDIUM

CROSS-REFERENCE TO RELATED APPLICATIONS

The application is a continuation under 35 U.S.C. § 120 of PCT Application No. PCT/CN2019/117098 filed on Nov. 11, 2019, which claims priority under 35 U.S.C. § 119(a) and/or PCT Article 8 to Chinese Patent Application No. 201910718497.3, filed on Aug. 5, 2019, the disclosures of which are hereby incorporated by reference in their entireties.

TECHNICAL FIELD

The application relates to the technical field of deep learning, in particular to a method and device for detecting and locating a lesion in a medical image, equipment and a storage medium.

BACKGROUND

Using an artificial intelligence algorithm to classify, recognize, detect, and locate different lesion signs in medical images can provide qualitative imaging indexes for clinical diagnosis. The conventional classification method based on deep learning can realize recognition of different lesion types, but cannot provide location information of suspected lesions. In a conventional target detection method based on deep learning, it is necessary to manually mark accurate box information in a lesion area of a sample image during model training. In addition, a number of sample images is often extremely large, usually more than 10,000, which results in a huge marking workload and makes it difficult to achieve rapid updating and learning of a model.

Therefore, it is an urgent problem for those skilled in the art to find a method that can realize the detection and localization of a lesion in a medical image with a small marking workload.

SUMMARY

Embodiments of the application provide a method and device for detecting and locating a lesion in a medical image, equipment and a storage medium.

A method for detecting and locating a lesion in a medical image includes the following operations.

A target medical image of a lesion to be detected is obtained.

The target medical image is input into a pre-trained deep learning model to obtain a target sequence output from the deep learning model, each element in the target sequence being a first confidence corresponding to each preset lesion type, the first confidence representing a probability that the target medical image belongs to a corresponding preset lesion type, the deep learning model being obtained by pre-training a medical image sample corresponding to each preset lesion type, and each medical image sample being marked with a lesion type included in the image.

After the target medical image is input into the deep learning model, a first feature map output from the last convolution layer in the deep learning model is extracted.

A weight value of each network unit corresponding to each preset lesion type in a fully connected layer of the deep learning model is extracted.

For each preset lesion type, a fusion feature map corresponding to each preset lesion type is calculated according to the first feature map and the weight value corresponding to each preset lesion type.

The fusion feature map corresponding to each preset lesion type is resampled to the size of the target medical image to generate a generic activation map corresponding to each preset lesion type.

The maximum connected area in the generic activation map corresponding to each preset lesion type is determined, and a mark border surrounding the maximum connected area is created, the maximum connected area referring to the connected area into which a point whose pixel value exceeds a specified pixel threshold falls in the generic activation map.

A mark border corresponding to each preset lesion type is added to the target medical image as a location result of the lesion to be detected.

A computer equipment includes a memory, a processor, and a computer readable instruction stored in the memory and capable of running on the processor. The processor, when executing the computer readable instruction, implements the steps of the method for detecting and locating a lesion in a medical image.

A readable storage medium stores a computer readable instruction, so that one or more processors performs the steps of the method for detecting and locating a lesion in a medical image.

The details of one or more embodiments of the application are set out in the drawings and descriptions below, and other features and advantages of the application will become apparent from the specification, the drawings, and the claims.

BRIEF DESCRIPTION OF THE DRAWINGS

In order to more clearly illustrate technical solutions in embodiments of the application, the drawings needed in the description of the embodiments are simply introduced below. It is apparent for those of ordinary skill in the art that the accompanying drawings in the following description are only some embodiments of the application, and some other accompanying drawings can also be obtained according to these on the premise of not contributing creative effort.

DETAILED DESCRIPTION OF THE EMBODIMENTS

The technical solutions in the embodiments of the application will be described clearly and completely below in combination with the drawings in the embodiments of the application. It is apparent that the described embodiments are not all embodiments but part of embodiments of the application. All other embodiments obtained by those of ordinary skill in the art based on the embodiments in the application without creative work shall fall within the scope of protection of the application.

Figure 1:
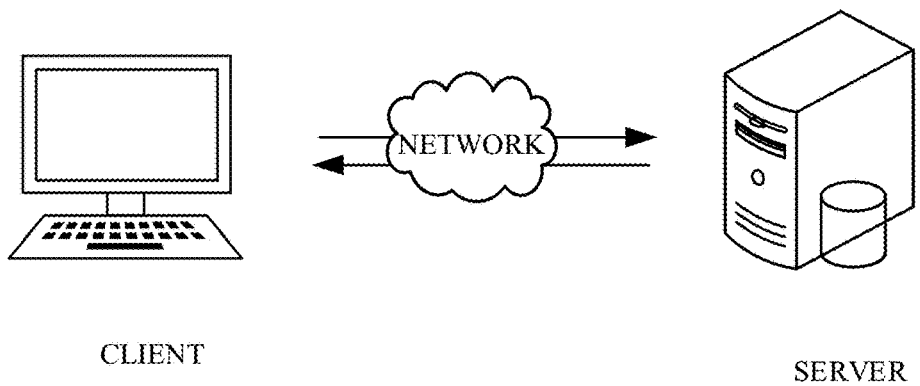
FIG. 1 is a schematic diagram of an application environment of a method for detecting and locating a lesion in a medical image according to an embodiment of the application.

A method for detecting and locating a lesion in a medical image provided in the application may be applied in the application environment as shown in FIG. 1. A client communicates with a server through a network. The client may be, but not limited to, a personal computer, a laptop, a smart phone, a tablet computer and a portable wearable device. The server may be realized by an independent server or a cluster of multiple servers.

Figure 2:
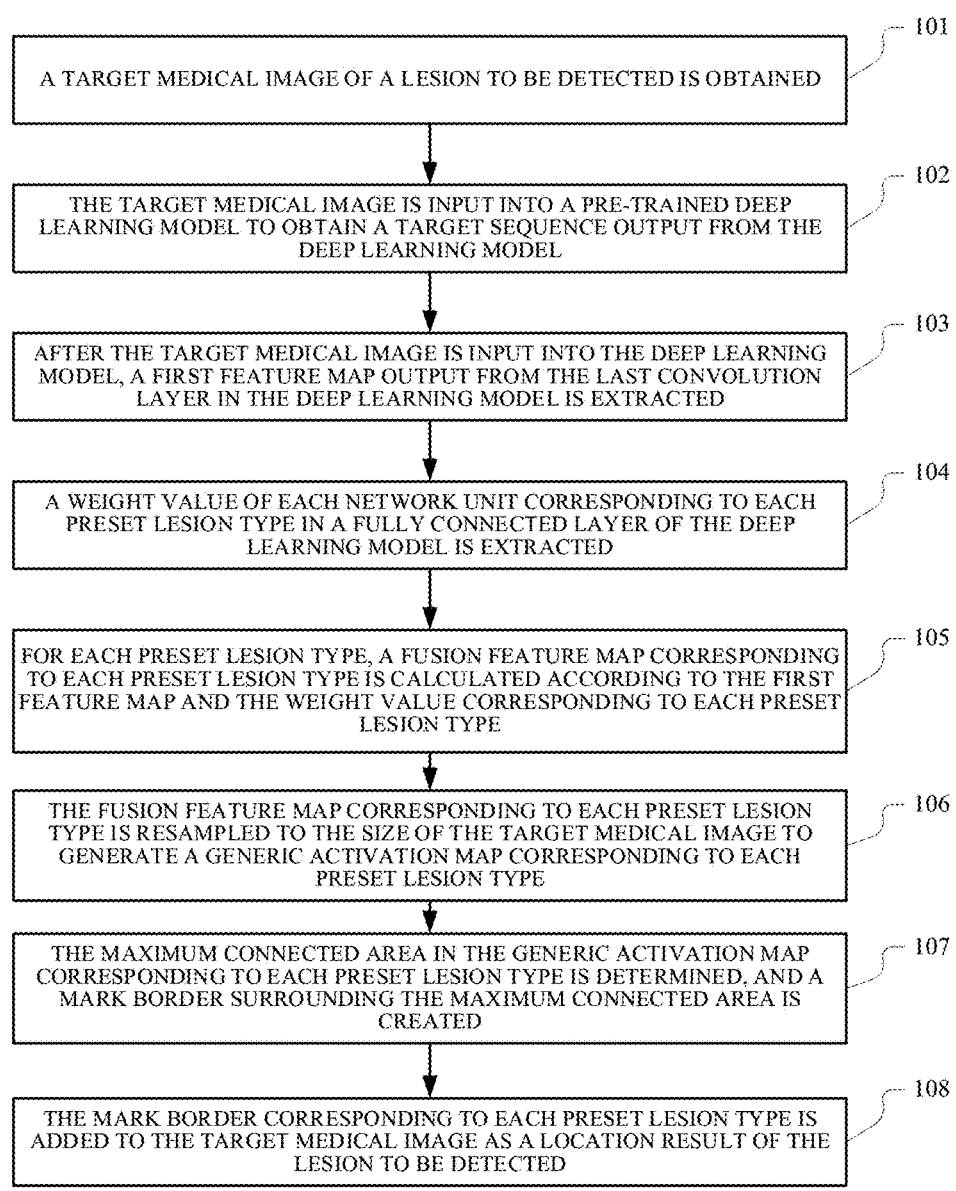
FIG. 2 is a flowchart of a method for detecting and locating a lesion in a medical image according to an embodiment of the application.

In an embodiment, as shown in FIG. 2, a method for detecting and locating a lesion in a medical image is provided. Illustrated by the application of the method to the server in FIG. 1, the method includes the following steps.

At S101, a target medical image of a lesion to be detected is obtained.

In the embodiment, first the server may obtain the target medical image of the lesion to be detected. The target medical image may be an Optical Coherence Tomography (OCT) image, a Computerized Tomography (CT) image, etc.

It is to be noted that the target medical image must have the same image type as a medical image sample used in the training of a deep learning model used later, or in the next S102, the deep learning model with a training sample that has the same image type as the target medical image is selected for recognition.

At S102, the target medical image is input into a pre-trained deep learning model to obtain a target sequence output from the deep learning model, each element in the target sequence being a first confidence corresponding to each preset lesion type, the first confidence representing a probability that the target medical image belongs to a corresponding preset lesion type, the deep learning model being obtained by pre-training a medical image sample corresponding to each preset lesion type, and each medical image sample being marked with a lesion type included in the image.

After obtaining the target medical image, the server may input the target medical image into the pre-trained deep learning model to obtain the target sequence output from the deep learning model. Each element in the target sequence corresponds to each preset lesion type through a fixed position. For example, assuming that there are four preset lesion types, which are respectively "pigment epithelial detachment", "retinal effusion", "vitreous membrane wart" and "epimacular membrane", and the target sequence is "0.8, 0.3, 0.2, 0.1", then the probability of positive pigment epithelial detachment is 0.8, the probability of positive "retinal effusion" is 0.3, the probability of positive "vitreous membrane wart" is 0.2, and the probability of positive "epimacular membrane" is 0.1.

It is to be noted that the target sequence is an intermediate concept, which mainly aims at deriving the first confidence and the relationship between the first confidence and the preset lesion type. For the deep learning model in the embodiment, its output is required to be the probability corresponding to the lesion type, so that the maximum connected area determined from a generic activation map, which is derived from a fusion feature map in the following steps, can be guaranteed to be the location of the lesion to be detected, that is, the location needing to be located in the solution.

Figure 3:
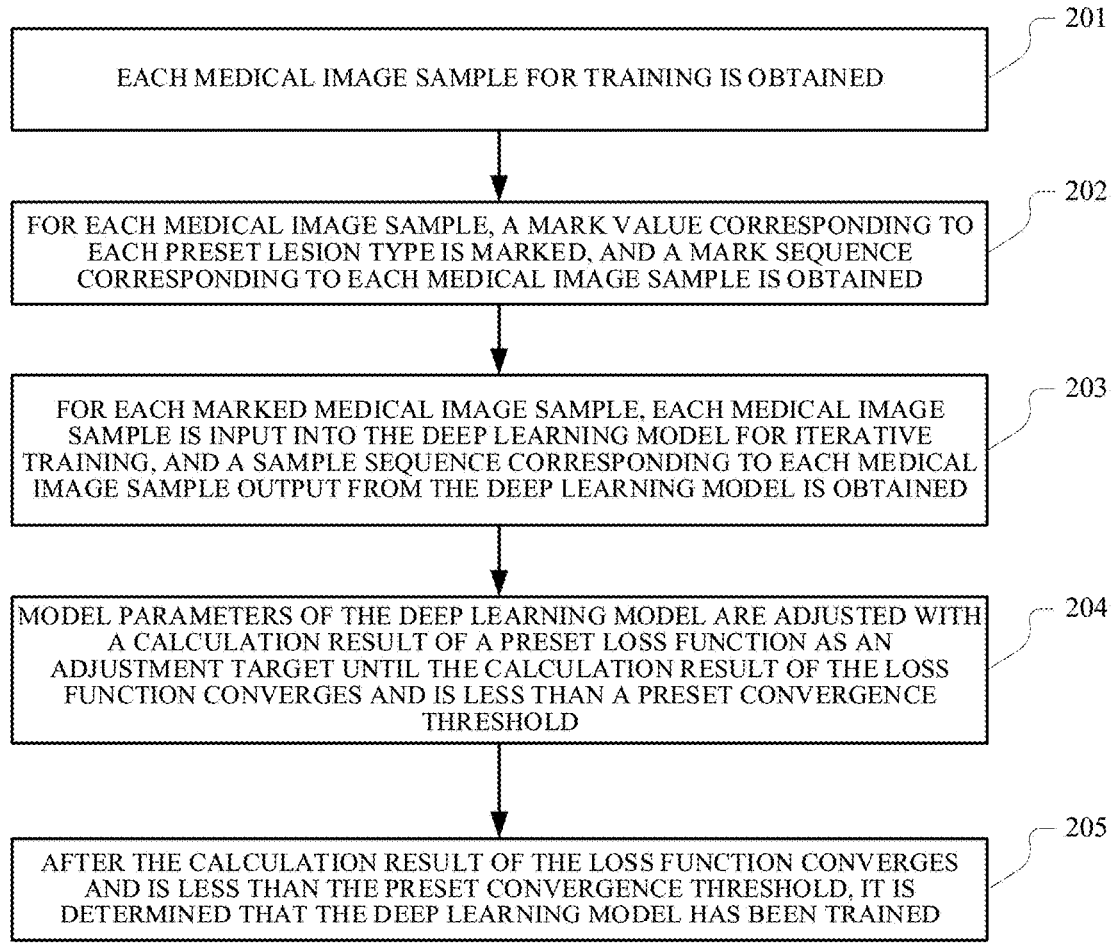
FIG. 3 is a flowchart of training a deep learning model using a method for detecting and locating a lesion in a medical image in an application scenario according to an embodiment of the application.

For the convenience of understanding, a pre-training process of the deep learning model will be described in detail below. Further, as shown in FIG. 3, the deep learning model is obtained by pre-training in the following steps.

At S201, each medical image sample for training is obtained.

At S202, for each medical image sample, a mark value corresponding to each preset lesion type is marked, and a mark sequence corresponding to each medical image sample is obtained, each element in the mark sequence being the mark value corresponding to each preset lesion type, and in each medical image sample, a mark value corresponding to the preset lesion type that is positive being 1, and a mark value corresponding to the preset lesion type that is negative being 0.

At S203, for each marked medical image sample, each medical image sample is input into the deep learning model for iterative training, and a sample sequence corresponding to each medical image sample output from the deep learning model is obtained, each element in the sample sequence being a second confidence corresponding to each preset lesion type, and the second confidence representing a probability that each medical image sample belongs to a corresponding preset lesion type.

At S204, model parameters of the deep learning model are adjusted with a calculation result of a preset loss function as an adjustment target until the calculation result of the loss function converges and is less than a preset convergence threshold, the loss function being used for calculating an error between the sample sequence and the mark sequence corresponding to each medical image sample.

At S205, after the calculation result of the loss function converges and is less than the preset convergence threshold, it is determined that the deep learning model has been trained.

For S201, before training, the server first obtains each medical image sample for training. These medical image samples may be collected in advance, but it is to be noted that the image type of these medical image samples must be consistent with that of the target medical image, that is, if the target medical image is an OCT image, then the medical image sample should also be an OCT image.

For S202, in the embodiment, each medical image sample is marked with a mark sequence in advance. Each element in the mark sequence is a mark value corresponding to each preset lesion type. The mark value corresponding to the preset lesion type that is positive is 1, and the mark value corresponding to the preset lesion type that is negative is 0. For example, assuming that a medical image sample, after recognized by a medical expert, shows a lesion "intra-retinal effusion" on it, there are a total of four preset lesion types, which are successively "pigment epithelial detachment", "retinal effusion", "vitreous membrane war" and "epimacular membrane", then the mark sequence of the medical image sample may be denoted as "0100".

It can be seen that the elements in the mark sequence correspond to the preset lesion types through the fixed positions, the values of the element are 0 or 1, 0 means the preset lesion type is negative, and 1 means the preset lesion type is positive.

Figure 4:
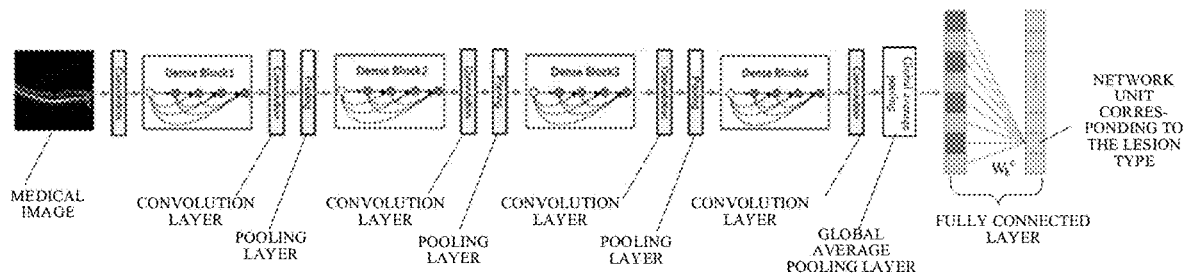
FIG. 4 is a schematic diagram of a network structure of a deep learning model according to an embodiment of the application.

For S203, further, with reference to FIG. 4, the deep learning model includes a preset first number of Dense Blocks and a fully connected layer. A convolution layer and a pooling layer are set between any two adjacent Dense Blocks, and a convolution layer and a global average pooling layer are set between the last Dense Block and the fully connected layer. The fully connected layer includes a preset second number of network units. The preset second number is equal to the number of preset lesion types. It is to be noted that the deep learning model in FIG. 4 is specifically equipped with 4 Dense Blocks. In actual use, the number of Dense Blocks may be increased or decreased according to the actual situation.

Based on the network structure of the deep learning model, S203 may specifically include: before each medical image sample is input into the deep learning model, the medical image sample is vectorized first and convolved for dimension reduction, and then the vector after dimension reduction is input into the first Dense Block. The first Dense Block performs multi-layer dense connected nonlinear transformation processing to the input vector, and convolves and pools a result obtained after processing, and then puts the result into the second Dense Block for processing. Similarly, the result obtained after the processing of the second Dense Block is convolved and pooled, and then put into the third Dense Block for processing; and so on, until the processing of the last Dense Block (FIG. 4 shows the fourth Dense Block), convolution and global average pooling are performed to the result obtained after the processing, and then the obtained vector is put into the fully connected layer for classification and recognition to obtain the value output by each network unit in the fully connected layer, that is, each second confidence and each element in the sample sequence. These elements constitute the sample sequence.

For each Dense Block in the deep learning model, after the vector is input into the Dense Block, the Dense Block includes multiple intensively connected processing layers, each of which may be represented by a nonlinear transformation function $H_1$). If the output of the first processing layer is x1, then $x1=H_l([x0, x1, \ldots, x(l-1)])$, where $[x0, x1, \ldots, x(l-1)]$ represents the output of the zeroth processing layer, $\ldots$, the $(l-1)$-th processing layer. It is understandable that the nonlinear transformation function $H_l(\bullet)$ in the embodiment may be specifically a compound function of three continuous operations, that is, Batch Normalization (BN), ReLU and Convolution (Conv).

For the fully connected layer, each network unit in the fully connected layer outputs a confidence a, which is expressed as $a=\delta(wx+b)$, where x is the input of the fully connected layer, w and b are a weight and a bias of the network unit respectively, and $\delta$ is specifically the sigmoid function $\delta(x)=1/(1+e^{-x})$.

For S203, it is to be noted that when the deep learning model is trained, it is necessary to repeatedly input all medical image samples into the deep learning model respectively for training, that is, iterative training, and the adjustment of model parameters of the deep learning model is completed in the iterative training process. It can be seen that the iterative training process of the deep learning model is processed in combination with S204. After the completion of iterative training, S204 is performed to determine whether a calculation result of the loss function has converged, so as to know whether the deep learning model has been trained (i.e., whether training of the deep learning model is completed).

For S204, it can be seen from the above content that in the iterative training process of the deep learning model, the server adjusts the model parameters of the deep learning model with the calculation result of the preset loss function as an adjustment target, until the calculation result of the loss function converges and is less than the preset convergence threshold. The loss function may be specifically a binary cross entropy loss function. The preset convergence threshold may be set according to the actual use, for example, it may be set to 0.005. Generally, the preset convergence threshold should be small enough to ensure that the calculation result of the loss function is small enough, so that the difference between an output value and a mark value of the model is within an acceptable range.

When the model parameters are adjusted, an Adam optimization method may be used to optimize the training process of the model. The learning rate of training may be set as lr=0.0001. Through the Adam optimization method, the model parameters of the deep learning model are automatically adjusted according to the calculation result of the loss function during this iteration training. After the model parameters are adjusted, the next iterative training process is performed and the result of the loss function is calculated, so as to perform the next adjustment of model parameters. After such repeated iterative training and adjustment of model parameters, the calculation result of the loss function may finally converge and be less than the preset convergence threshold. At this point, it may be determined that the deep learning model has been trained.

In addition, optionally, the order of inputting the medical image samples may be randomly scrambled in the training process to achieve a better iterative training effect.

For S205, it can be seen that after the calculation result of the loss function converges, the server may determine that the deep learning model has been trained.

At S103, after the target medical image is input into the deep learning model, a first feature map output from the last convolution layer in the deep learning model is extracted.

In combination with FIG. 4, it can be seen that the last (or final) convolution layer of the deep learning model outputs a vector feature map, and the server may extract the vector feature map as the first feature map.

At s104, a weight value of each network unit corresponding to each preset lesion type in a fully connected layer of the deep learning model is extracted.

The fully connected layer of the deep learning model includes multiple network units. The number of these network units is equal to the number of preset lesion types, and the network unit is used for classification and identification of the vector feature map input into the fully connected layer. Therefore, it is understandable that the weight value pre-adjusted during training in each network unit may be considered as the quantification of importance of the corresponding preset lesion type on the vector feature map, so the server can extract the weight value of each network unit corresponding to each preset lesion type in the fully connected layer of the deep learning model.

At S105, for each preset lesion type, a fusion feature map corresponding to each preset lesion type is calculated according to the first feature map and the weight value corresponding to each preset lesion type.

After obtaining the first feature map and the weight value of each network unit, for each preset lesion type, the server may calculate the fusion feature map corresponding to each preset lesion type according to the first feature map and the weight value corresponding to each preset lesion type.

Further, S105 may specifically include that: for each preset lesion type, the first feature map and the weight value corresponding to each preset lesion type are put into a preset weighted sum formula to calculate the fusion feature map corresponding to each preset lesion type.

The weighted sum formula is:

$$F_c = \sum_{k=1}^{K} w_k^c \cdot f_k,$$

where $F_c$ is a vector value of the fusion feature map, K is the number of first feature maps extracted, c is the number of the preset lesion type, $f_k$ represents the k-th first feature map extracted, $w_k^c$ represents the weight of the c-th preset lesion type corresponding to the k-th input unit in the fully connected layer.

It can be seen that in the calculated fusion feature map, the pixel value of each point reflects the possibility that the point belongs to the preset lesion type, and the greater the pixel value, the greater the possibility.

At S106, the fusion feature map corresponding to each preset lesion type is resampled to the size of the target medical image to generate a generic activation map corresponding to each preset lesion type.

In order to keep the size of the fusion feature map consistent with the size of the target medical image, the server may resample the fusion feature map corresponding to each preset lesion type to the size of the target medical image to generate the generic activation map corresponding to each preset lesion type, so that the border determined later in the generic activation map is applicable to the target medical image.

At S107, the maximum connected area in the generic activation map corresponding to each preset lesion type is determined, and a mark border surrounding the maximum connected area is created, the maximum connected area referring to the connected area into which a point whose pixel value exceeds a specified pixel threshold falls in the generic activation map.

In the embodiment, the specified pixel threshold may be preset as a boundary value for defining the points belonging to a lesion area in the generic activation map. Therefore, the server may determine the maximum connected area in the generic activation map corresponding to each preset lesion type, and creates the mark border surrounding the maximum connected area. The maximum connected area refers to the connected area into which the point whose pixel value exceeds the specified pixel threshold falls in the generic activation map. It is understandable that the mark border surrounds the maximum connected area which includes points that satisfy a condition (that is, the pixel value exceeds the specified pixel threshold), so it may be considered that the maximum connected area is the lesion area of the preset lesion type, and then the mark border marks the lesion area from the generic activation map.

It is to be noted that the specified pixel threshold may be set either artificially or according to the maximum pixel value on the generic activation map, for example, it is set to 20% of the maximum pixel value.

Figure 5:
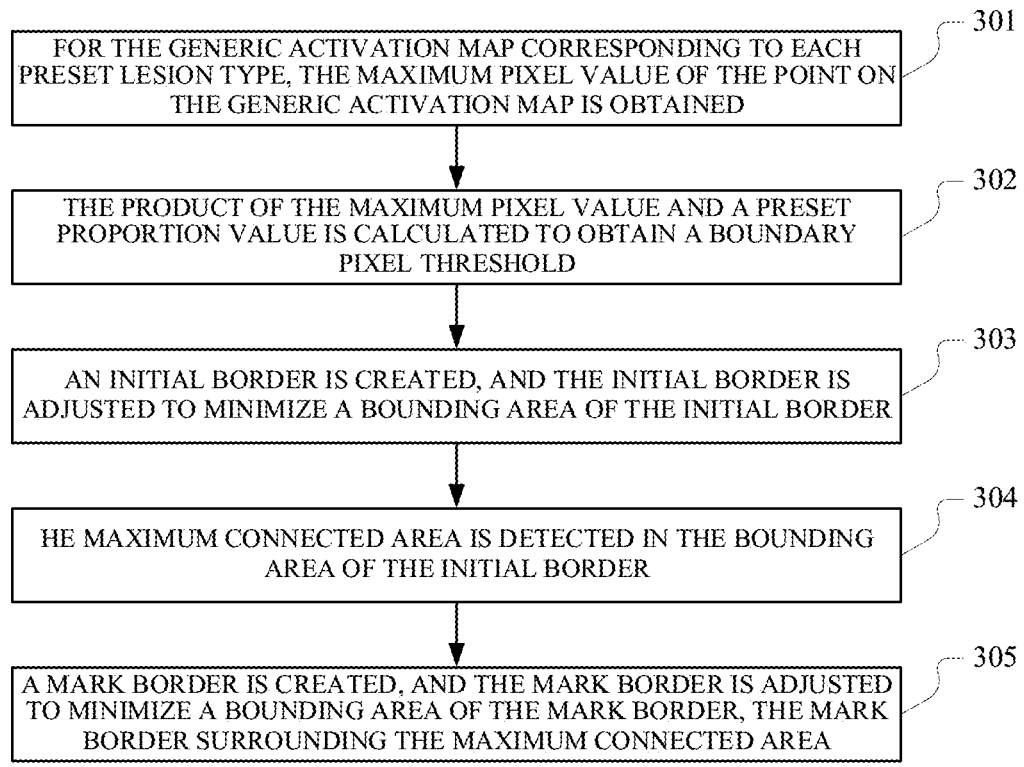
FIG. 5 is a flowchart of a method for detecting and locating a lesion in a medical image in an application scenario according to an embodiment of the application.

For convenience of understanding, the content about how to determine the maximum connected area from the generic activation map and create the mark border will be described in detail below. Further, as shown in FIG. 5, S107 may include the following steps.

At S301, for the generic activation map corresponding to each preset lesion type, the maximum pixel value of the point on the generic activation map is obtained.

At S302, the product of the maximum pixel value and a preset proportion value is calculated to obtain a boundary pixel threshold, the preset proportion value being greater than 0 and less than 1.

At S303, an initial border is created, and the initial border is adjusted to minimize a bounding area of the initial border, the initial border surrounding all points whose pixel value is greater than the boundary pixel threshold on the generic activation map.

At S304, the maximum connected area is detected in the bounding area of the initial border.

At S305, a mark border is created, and the mark border is adjusted to minimize a bounding area of the mark border, the mark border surrounding the maximum connected area.

First, it is to be noted that in all the subsequent steps, the generic activation map corresponding to each preset lesion type is processed separately. Specifically, the server may process multiple generic activation maps simultaneously in a multi-threaded manner, and one thread calculates and processes one generic activation map, and may also perform S301 to S305 on each generic activation map individually in a single-threaded manner, which is not limited in the embodiment.

For S301, for the generic activation map corresponding to each preset lesion type, the server may obtain the maximum pixel value of the points on the generic activation map, that is, the maximum of pixel values of all the points.

For S302, a preset proportion value may be preset. After the maximum pixel value is obtained, the server may calculate the product of the maximum pixel value and the boundary pixel threshold. The preset proportion value is greater than 0 and less than 1, for example, it may be set to 0.2 or 20%.

For S303, after the boundary pixel threshold is calculated, the server may first create an initial border, which surrounds all the points whose pixel value is greater than the boundary pixel threshold on the generic activation map. Then, the server adjusts the initial border to minimize the bounding area of the initial border, which is equivalent to the minimum border that can surround all the above points.

For S304, after determining the minimized initial border, the server may detect the maximum connected area in the bounding area of the initial border. It is understandable that the representation of lesion on the image should be a whole connected area, while in the area limited by the initial border, the maximum connected area must be the lesion area. Therefore, the detection of the maximum connected area is equivalent to finding the lesion area.

It is to be noted that there are many ways to detect the maximum connected area. For example, the bwlabel function in matlab to solve the connected area of the image may be used, the findCoutours function in OpenCV may also be used, etc. The embodiment does not make a specific limit to this.

For S305, after detecting the maximum connected area, the server may create a mark border, which surrounds the maximum connected area, and then adjusts the mark border to minimize the bounding area of the mark border, so that a minimum mark border surrounding the maximum connected area may be obtained, and the mark border plays the role of marking the lesion area.

Specifically, the initial border and the mark border in the embodiment may be rectangular borders, other polygonal borders, or even irregular borders.

At S108, the mark border corresponding to each preset lesion type is added to the target medical image as a location result of the lesion to be detected.

After the mark border is created, it is understandable that because the generic activation map has the same size as the target medical image, and is from the target medical image, the area selected by the mark border on the generic activation map is the area of the lesion on the target medical image. Therefore, the server may add the mark border corresponding to the preset lesion type on the target medical image to complete the marking of the preset lesion type. Similarly, the server creates all the mark borders of the preset lesion types and adds them on the same target medical image, then all lesion areas on the target medical image may be selected with the mark border, which realizes the detection and location of the lesion area.

Figure 6:
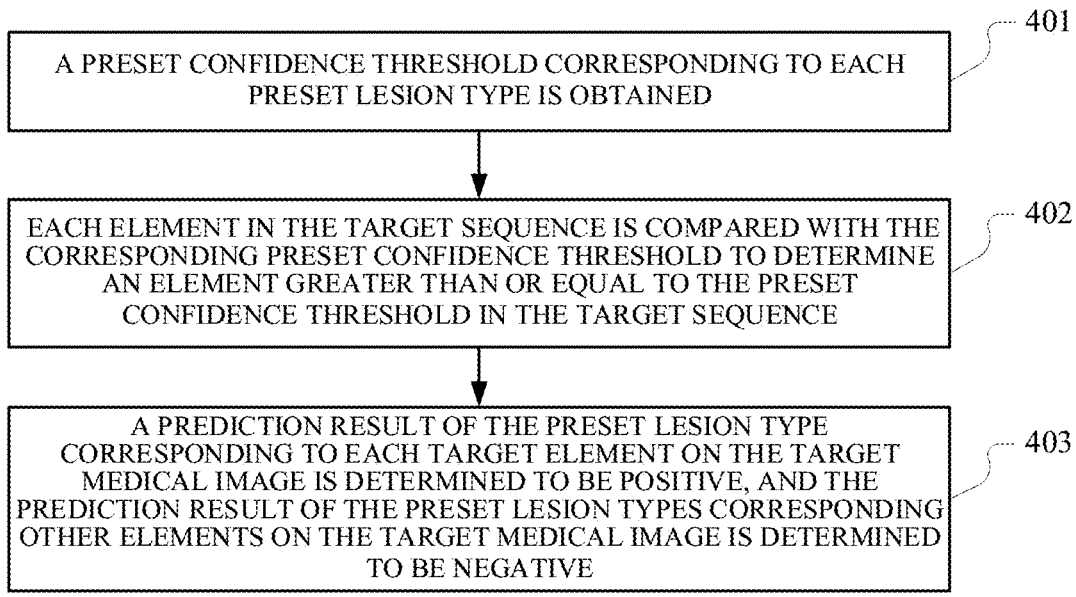
FIG. 6 is a flowchart of differentiating positive/negative lesions using a method for detecting and locating a lesion in a medical image in an application scenario according to an embodiment of the application.

Considering that the server performs S102 to obtain each first confidence, and these first confidences only represent the probability that the target medical image belongs to the corresponding preset lesion type, it is difficult for the user to directly know whether the target medical image has a lesion and which lesions it has from these first confidences. Therefore, in the embodiment, after each first confidence is obtained, a preset confidence threshold may be used to determine which lesions are positive and which lesions are negative in the target medical image, so as to be convenient for users to consult and obtain classification results. Further, as shown in FIG. 6, after S102, the method further includes the following steps.

At S401, a preset confidence threshold corresponding to each preset lesion type is obtained.

At S402, each element in the target sequence is compared with the corresponding preset confidence threshold to determine an element greater than or equal to the preset confidence threshold in the target sequence, and the element is denoted as a target element.

At S403, a prediction result of the preset lesion type corresponding to each target element on the target medical image is determined to be positive, and the prediction result of the preset lesion types corresponding other elements on the target medical image is determined to be negative, the other elements referring to the elements in the target sequence other than the target element.

For S401, in the embodiment, the preset confidence thresholds corresponding to the preset lesion types may be preset on the server, and the server may obtain these preset confidence thresholds when needed.

It is understandable that these preset confidence thresholds may be set artificially based on empirical values or determined in advance through samples. A method for predetermining the preset confidence threshold through samples will be described in detail below.

Figure 7:
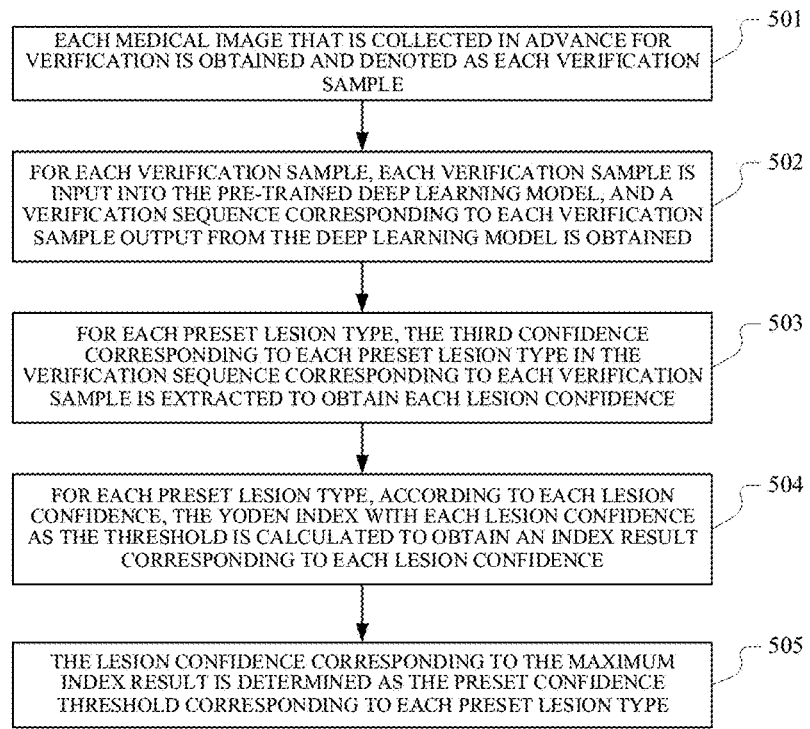
FIG. 7 is a flowchart of measuring a preset confidence threshold using a method for detecting and locating a lesion in a medical image in an application scenario according to an embodiment of the application.

Further, as shown in FIG. 7, the preset confidence threshold corresponding to each preset lesion type is predetermined in the following steps.

At S501, each medical image that is collected in advance for verification is obtained and denoted as each verification sample.

At S502, for each verification sample, each verification sample is input into the pre-trained deep learning model, and a verification sequence corresponding to each verification sample output from the deep learning model is obtained, each element in the verification sequence being a third confidence corresponding to each preset lesion type, and the third confidence representing a probability that each verification sample belongs to a corresponding preset lesion type.

At S503, for each preset lesion type, the third confidence corresponding to each preset lesion type in the verification sequence corresponding to each verification sample is extracted to obtain each lesion confidence.

At S504, for each preset lesion type, according to each lesion confidence, the Yoden index with each lesion confidence as the threshold is calculated to obtain an index result corresponding to each lesion confidence.

At S505, the lesion confidence corresponding to the maximum index result is determined as the preset confidence threshold corresponding to each preset lesion type, the maximum index result referring to the maximum of the index results corresponding to the confidences of lesion.

For S501, similar to S201, some medical images may be collected in advance as samples for verification, and denoted as verification samples.

For S502, for each verification sample, the server may input each verification sample into the pre-trained deep learning model to obtain a verification sequence corresponding to each verification sample output from the deep learning model, each element in the verification sequence being the third confidence corresponding to each preset lesion type, and the third confidence representing the probability that each verification sample belongs to the corresponding preset lesion type. The processing process of each verification sample in the deep learning model is similar to the above content, so it will not be repeated here.

For S503, it is understandable that if there are N verification samples input into the deep learning model, then N verification sequences are obtained in S502. Therefore, for each preset lesion type, the server may extract the third confidence corresponding to the preset lesion type from the N verification sequences and obtain a total of N third confidences, that is, N lesion confidences.

For S504, for each preset lesion type, after obtaining the N lesion confidences corresponding to the preset lesion types, the server may determine each lesion confidence as each threshold, and calculate the Youden index of each lesion confidence for each threshold to obtain the index result corresponding to the threshold. It can be seen that if there are a total of N lesion confidences, then there are a total of N thresholds, and one index result is calculated for each threshold. Therefore, N index results are respectively calculated for N thresholds.

For example, assuming that for a certain preset lesion type, the N lesion confidences obtained by the server are denoted as $l=\{l_1, l_2, l_3, \ldots\}$, the Youden indexes, when $l_1$, $l_2$, $l_3$, ... are taken as the threshold, are calculated respectively. The detailed steps are as follows:

taking $l_1$ as the threshold, each verification sample is predicted to obtain a prediction result (being positive when the confidence is greater than or equal to $l_1$, and being negative when the confidence is less than $l_1$) of each verification sample; the prediction result is compared with a marked result of the verification sample to count the number of true positive samples, false positive samples, true negative samples and false negative samples, so as to calculate a True Positive Rate (TPR) value and a False Positive Rate (TNR) value; the Youden index with $l_1$ as the threshold is calculated through the formula TPR+TNR−1 and denoted as $y_1$; and similarly, the Youden indexes $y_2, y_3, \ldots y_n$ with $l_2$, $l_3, \ldots$ as the threshold are calculated.

For S505, the N index results are compared, and the lesion confidence corresponding to the maximum value in the index results is taken as the preset confidence threshold corresponding to the preset lesion type. It is understandable that the Youden index is an indicator to evaluate the authenticity of screening test. The greater the index is, the better the effect of screening test is, that is, the more reliable the corresponding confidence is, the greater the authenticity is. Therefore, it may be considered that the lesion confidence corresponding to the maximum value of the Yoden index is a reliable confidence boundary value.

It can be seen from the above content that the preset confidence threshold corresponding to each preset lesion type may be obtained by performing the above steps for each preset lesion type.

For S402, the confidence in the embodiment represents the probability that the medical image belongs to the corresponding preset lesion type, that is, the probability that the preset lesion type is positive in the medical image. Therefore, the server compares each element in the target sequence with the corresponding preset confidence threshold. If a certain element is greater than the corresponding preset confidence threshold, it indicates that the preset lesion type corresponding to the element is positive; conversely, it indicates that the preset lesion type corresponding to the element is negative. In the embodiment, the element greater than or equal to the preset confidence threshold in the target sequence may be first determined as the target element.

For S403, it can be seen from the above content that the server may determine the prediction result of the preset lesion type corresponding to each target element on the target medical image to be positive, and determine the prediction result of the preset lesion types corresponding other elements on the target medical image to be negative, the other elements referring to the elements in the target sequence other than the target element.

In the embodiments of the application, first, the target medical image of the lesion to be detected is obtained; second, the target medical image is input into the pre-trained deep learning model to obtain the target sequence output from the deep learning model, each element in the target sequence being the first confidence corresponding to each preset lesion type, the first confidence representing the probability that the target medical image belongs to the corresponding preset lesion type, the deep learning model being obtained by pre-training a medical image sample corresponding to each preset lesion type, and each medical image sample being marked with the lesion type included in the image; after the target medical image is input into the deep learning model, the first feature map output from the last convolution layer in the deep learning model is extracted; and the weight value of each network unit corresponding to each preset lesion type in the fully connected layer of the deep learning model is extracted; next, for each preset lesion type, the fusion feature map corresponding to each preset lesion type is calculated according to the first feature map and the weight value corresponding to each preset lesion type; next, the fusion feature map corresponding to each preset lesion type is resampled to the size of the target medical image to generate the generic activation map corresponding to each preset lesion type; after that, the maximum connected area in the generic activation map corresponding to each preset lesion type is determined, and the mark border surrounding the maximum connected area is created, the maximum connected area referring to the connected area into which the point whose pixel value exceeds the specified pixel threshold falls in the generic activation map; at last, the mark border corresponding to each preset lesion type is added to the target medical image as the location result of the lesion to be detected. It can be seen that the deep learning model trained in the application does not need to mark the accurate location information of the lesions, but only the lesion types included in each sample, which greatly reduces the marking workload and improves the ability of the deep learning model to update and learn quickly. In addition, the application can not only classify and recognize the lesion type in the target medical image through the deep learning model, but also detect and locate the lesions in the target medical image through the first feature map generated in the recognition process of the deep learning model, and mark them out in the form of border, so as to realize the detection and location of the lesions in the medical image.

It should be understood that, in the above embodiments, a magnitude of a sequence number of each step does not mean an execution sequence and the execution sequence of each process should be determined by its function and an internal logic and should not form any limit to an implementation process of the embodiments of the disclosure.

Figure 8:
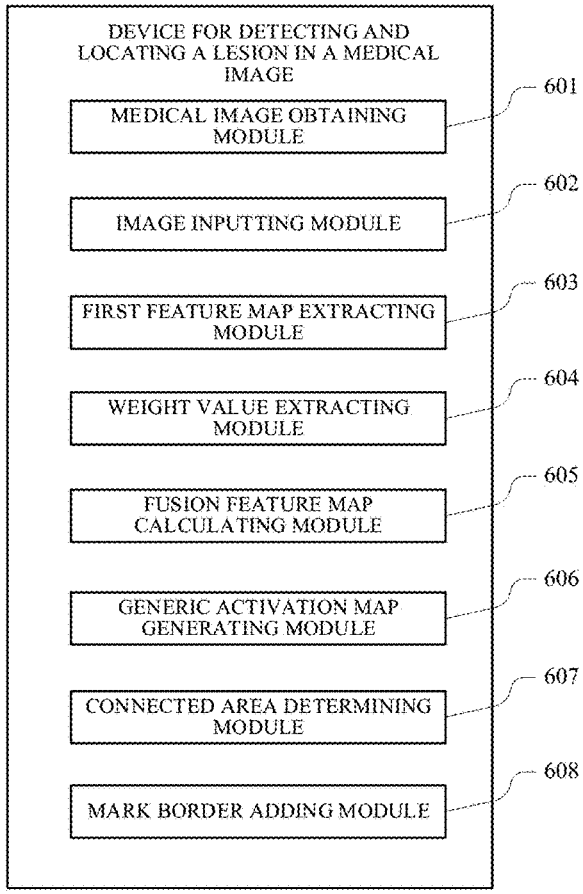
FIG. 8 is a structure diagram of a device for detecting and locating a lesion in a medical image in an application scenario according to an embodiment of the application.

In an embodiment, a device for detecting and locating a lesion in a medical image is provided, which corresponds to the method for detecting and locating a lesion in a medical image in the above embodiment. As shown in FIG. 8, the device for detecting and locating a lesion in a medical image includes a medical image obtaining module 601, an image inputting module 602, a first feature map extracting module 603, a weight value extracting module 604, a fusion feature map calculating module 605, a generic activation map generating module 606, a connected area determining module 607 and a mark border adding module 608. Each functional module is described in detail below.

The medical image obtaining module 601 is configured to obtain the target medical image of the lesion to be detected.

The image inputting module 602 is configured to input the target medical image into the pre-trained deep learning model to obtain the target sequence output from the deep learning model, each element in the target sequence being a first confidence corresponding to each preset lesion type, the first confidence representing a probability that the target medical image belongs to a corresponding preset lesion type, the deep learning model being obtained by pre-training the medical image sample corresponding to each preset lesion type, and each medical image sample being marked with a lesion type included in the image.

The first feature map extracting module 603 is configured to, after the target medical image is input into the deep learning model, extract the first feature map output from the last convolution layer in the deep learning model.

The weight value extracting module 604 is configured to extract the weight value of each network unit corresponding to each preset lesion type in the fully connected layer of the deep learning model.

The fusion feature map calculating module 605 is configured to, for each preset lesion type, calculate the fusion feature map corresponding to each preset lesion type according to the first feature map and the weight value corresponding to each preset lesion type.

The generic activation map generating module 606 is configured to resample the fusion feature map corresponding to each preset lesion type to the size of the target medical image to generate the generic activation map corresponding to each preset lesion type.

The connected area determining module 607 is configured to determine the maximum connected area in the generic activation map corresponding to each preset lesion type, and create the mark border surrounding the maximum connected area, the maximum connected area referring to the connected area into which the point whose pixel value exceeds the specified pixel threshold falls in the generic activation map.

The mark border adding module 608 is configured to add the mark border corresponding to each preset lesion type to the target medical image as the location result of the lesion to be detected.

Figure 9:
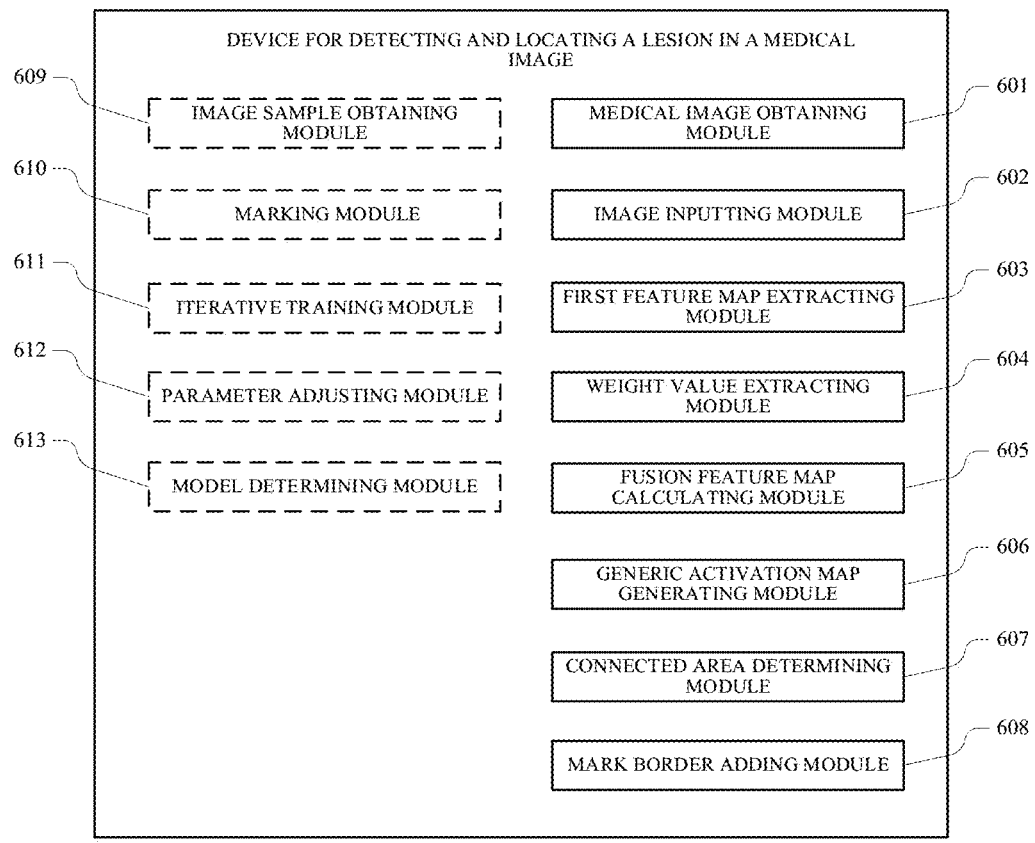
FIG. 9 is a structure diagram of a device for detecting and locating a lesion in a medical image in another application scenario according to an embodiment of the application.

As shown in FIG. 9, further, the deep learning model may be obtained by pre-training through the following modules:
an image sample obtaining module 609, configured to obtain each medical image sample for training;
a marking module 610, configured to, for each medical image sample, mark the mark value corresponding to each preset lesion type, and obtain the mark sequence corresponding to each medical image sample, each element in the mark sequence being the mark value corresponding to each preset lesion type, and in each medical image sample, a mark value corresponding to the preset lesion type that is positive being 1, and a mark value corresponding to the preset lesion type that is negative being 0;
an iterative training module 611 configured to, for each marked medical image sample, input each medical image sample into the deep learning model for iterative training, and obtain the sample sequence corresponding to each medical image sample output from the deep learning model, each element in the sample sequence being a second confidence corresponding to each preset lesion type, and the second confidence representing a probability that each medical image sample belongs to a corresponding preset lesion type;
a parameter adjusting module 612, configured to adjust the model parameters of the deep learning model with the calculation result of the preset loss function as the adjustment target until the calculation result of the loss function converges and is less than the preset convergence threshold, the loss function being used for calculating the error between the sample sequence and the mark sequence corresponding to each medical image sample; and
a model determining module 613, configured to, after the calculation result of the loss function converges and is less than the preset convergence threshold, determine that the deep learning model has been trained.

Figure 10:
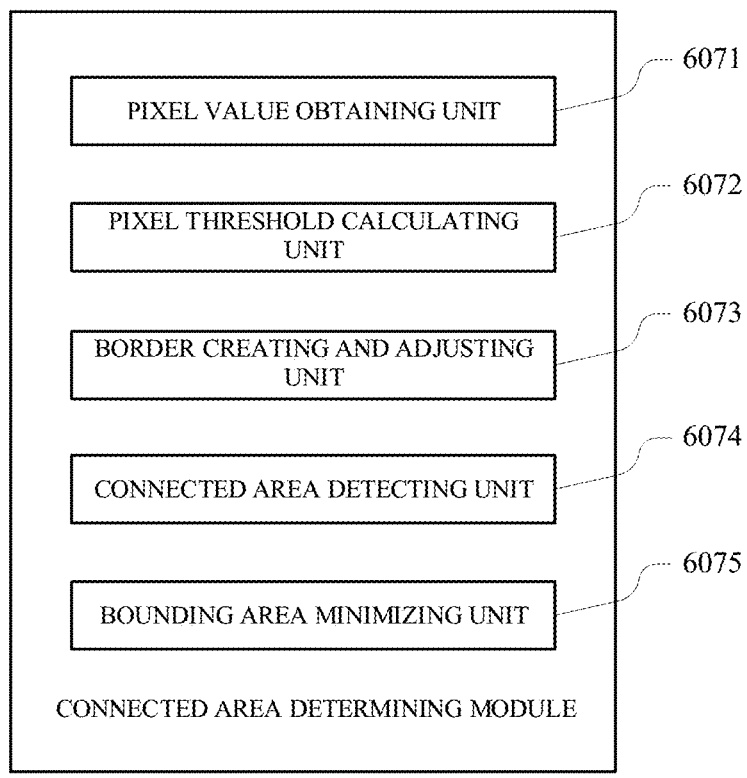
FIG. 10 is a structure diagram of a connected area determining module according to an embodiment of the application.

As shown in FIG. 10, further, the connected area determining module 607 may include:
a pixel value obtaining unit 6071, configured to, for the generic activation map corresponding to each preset lesion type, obtain the maximum pixel value of the point on the generic activation map;
a pixel threshold calculating unit 6072, configured to calculate the product of the maximum pixel value and the preset proportion value to obtain the boundary pixel threshold, the preset proportion value being greater than 0 and less than 1;
a border creating and adjusting unit 6073, configured to create an initial border, and adjust the initial border to minimize the bounding area of the initial border, the initial border surrounding all points whose pixel value is greater than the boundary pixel threshold on the generic activation map;
a connected area detecting unit 6074, configured to detect the maximum connected area in the bounding area of the initial border; and
a bounding area minimizing unit 6075, configured to create the mark border, and adjust the mark border to minimize the bounding area of the mark border, the mark border surrounding the maximum connected area.

Further, the device for detecting and locating a lesion in a medical image may further include a confidence threshold obtaining module, a comparing module and a prediction result determining module.

The confidence threshold obtaining module is configured to obtain the preset confidence threshold corresponding to each preset lesion type.

The comparing module is configured to compare each element in the target sequence with the corresponding preset confidence threshold to determine an element greater than or equal to the preset confidence threshold in the target sequence, and denote it as the target element.

The prediction result determining module is configured to determine the prediction result of the preset lesion type corresponding to each target element on the target medical image to be positive, and determine the prediction result of the preset lesion types corresponding other elements on the target medical image to be negative, the other elements referring to the elements in the target sequence other than the target element.

Further, the preset confidence threshold corresponding to each preset lesion type may be predetermined through the following modules:
a verification sample obtaining module, configured to obtain each medical image that is collected in advance for verification and denote it as each verification sample;
a sample inputting module, configured to, for each verification sample, input each verification sample into the pre-trained deep learning model, and obtain the verification sequence corresponding to each verification sample output from the deep learning model, each element in the verification sequence being a third confidence corresponding to each preset lesion type, and the third confidence representing a probability that each verification sample belongs to a corresponding preset lesion type;
a lesion confidence extracting module, configured to, for each preset lesion type, extract the third confidence corresponding to each preset lesion type in the verification sequence corresponding to each verification sample to obtain each lesion confidence;
an index result calculating module, configured to, for each preset lesion type, according to each lesion confidence, calculate the Yoden index with each lesion confidence as the threshold to obtain the index result corresponding to each lesion confidence; and
a threshold determining module, configured to determine the lesion confidence corresponding to the maximum index result as the preset confidence threshold corresponding to each preset lesion type, the maximum index result referring to the maximum of the index results corresponding to the confidences of lesion.

For specific limitations of the device for detecting and locating a lesion in a medical image, the above limitations of the method for detecting and locating a lesion in a medical image may be referred to, which will not be repeated here. Each module in the device for detecting and locating a lesion in a medical image may be realized in whole or in part by software, hardware and their combination. Each above module may be embedded in or independent of a processor in computer equipment in the form of hardware, or stored in a memory in the computer equipment in the form of software, so that the processor may call and perform the operation corresponding to each module above.

Figure 11:
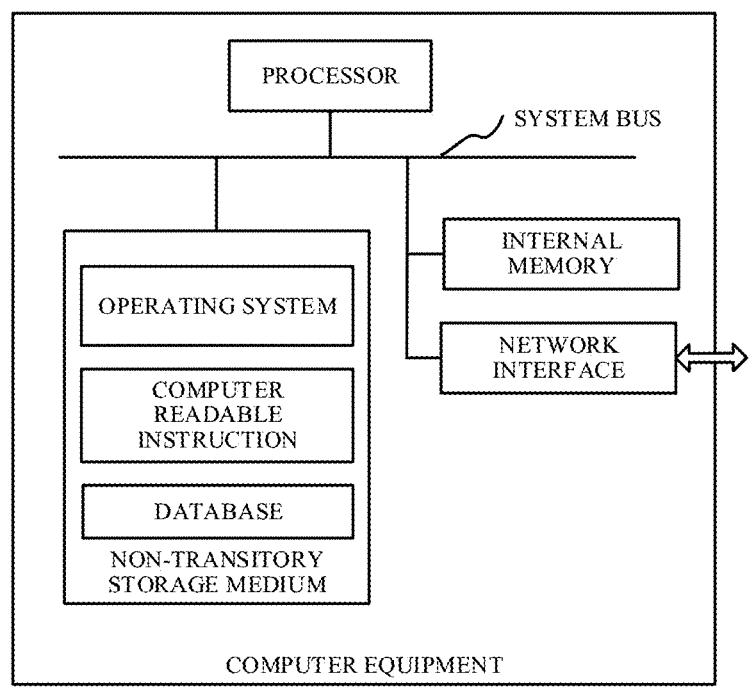
FIG. 11 is a schematic diagram of computer equipment according to an embodiment of the application.

In an embodiment, computer equipment is provided. The computer equipment may be a server, and its internal structure may be shown in FIG. 11. The computer equipment includes a processor, a memory, a network interface, and a database connected through a system bus. The processor of the computer equipment is used to provide computing and control capabilities. The memory of the computer equipment includes a readable storage medium and an internal memory. The readable storage medium stores an operating system, a computer readable instruction, and a database. The internal memory provides an environment for the operation of the operating system and the computer readable instruction in the readable storage medium. The database of the computer equipment is used for storing the data involved in the method for detecting and locating a lesion in a medical image. The network interface of the computer equipment is used to communicate with an external terminal through a network connection. The computer readable instruction, when executed by the processor, implements a method for detecting and locating a lesion in a medical image. The readable storage medium provided in the embodiment includes a non-volatile readable storage medium and a volatile readable storage medium.

In an embodiment, computer equipment is provided, which includes: a memory, a processor, and a computer readable instruction stored in the memory and capable of running on the processor. The processor, when executing the computer readable instruction, implements the steps, such as S101 to S108 shown in FIG. 2, of the method for detecting and locating a lesion in a medical image. Or, the processor, when executing the computer readable instruction, realizes the functions of the modules/units of the device for detecting and locating a lesion in a medical image, such as the functions of the modules 601 to the modules 608. In order to avoid repetition, the above will not be described herein in detail.

In an embodiment, one or more computer-readable storage media storing a computer readable instruction are provided. The computer readable instruction, when executed by one or more processors, enables the one or more processors to perform the steps of the method for detecting and locating a lesion in a medical image; or, the computer readable instruction, when executed by one or more processors, enables the one or more processors to realize the functions of the modules/units in the device for detecting and locating a lesion in a medical image. In order to avoid repetition, the above will not be described herein in detail. The readable storage medium provided in the embodiment includes a non-volatile readable storage medium and a volatile readable storage medium.

The above embodiments are only used for illustrating, but not limiting, the technical solutions of the disclosure. Although the disclosure is elaborated referring to the above embodiments, those of ordinary skill in the art should understand that they may still modify the technical solutions in each above embodiment, or equivalently replace a part of technical features; but these modifications and replacements do not make the nature of the corresponding technical solutions depart from the spirit and scope of the technical solutions in each embodiment of the disclosure, and these modifications and replacements should be included in the scope of protection of the disclosure.

What is claimed is:

1. A method for detecting and locating a lesion in a medical image, the method comprising:

obtaining a target medical image of a lesion to be detected;

inputting the target medical image into a pre-trained deep learning model to obtain a target sequence output from the deep learning model, wherein each element in the target sequence is a first confidence corresponding to each preset lesion type, wherein the first confidence represents a probability that the target medical image belongs to a corresponding preset lesion type, wherein the deep learning model is obtained by pre-training a medical image sample corresponding to each preset lesion type, and wherein each medical image sample is marked with a lesion type comprised in the target medical image;

after inputting the target medical image into the deep learning model, extracting a first feature map output from a last convolution layer in the deep learning model;

extracting a weight value of each network unit corresponding to each preset lesion type in a fully connected layer of the deep learning model;

for each preset lesion type, calculating a fusion feature map corresponding to each preset lesion type according to the first feature map and the weight value corresponding to each preset lesion type;

resampling the fusion feature map corresponding to each preset lesion type to a size of the target medical image to generate a generic activation map corresponding to each preset lesion type;

determining a maximum connected area in the generic activation map corresponding to each preset lesion type, and creating a mark border surrounding the maximum connected area, wherein the maximum connected area refers to a connected area into which a point whose pixel value exceeds a specified pixel threshold falls in the generic activation map; and adding a mark border corresponding to each preset lesion type to the target medical image as a location result of the lesion to be detected;

the method further comprising after inputting the target medical image into the pre-trained deep learning model to obtain the target sequence output from the deep learning model:

obtaining a preset confidence threshold corresponding to each preset lesion type;

comparing each element in the target sequence with the corresponding preset confidence threshold to determine an element greater than or equal to the preset confidence threshold in the target sequence, and denoting it as a target element; and determining a prediction result of the preset lesion type corresponding to each target element on the target medical image to be positive, and determining the prediction result of the preset lesion types corresponding other elements on the target medical image to be negative, wherein the other elements refer to the elements in the target sequence other than the target element; and the preset confidence threshold corresponding to each preset lesion type being predetermined as follows:
    obtaining each medical image that is collected in advance for verification and denoting it as each verification sample;
    for each verification sample, inputting each verification sample into the pre-trained deep learning model, and obtaining a verification sequence corresponding to each verification sample output from the deep learning model, wherein each element in the verification sequence is a third confidence corresponding to each preset lesion type, and wherein the third confidence represents a probability that each verification sample belongs to a corresponding preset lesion type;
    for each preset lesion type, extracting the third confidence corresponding to each preset lesion type in the verification sequence corresponding to each verification sample to obtain each lesion confidence;
    for each preset lesion type, according to each lesion confidence, calculating a Yoden index with each lesion confidence as a threshold to obtain an index result corresponding to each lesion confidence; and
    determining the lesion confidence corresponding to the maximum index result as the preset confidence threshold corresponding to each preset lesion type, wherein the maximum index result refers to the maximum of the index results corresponding to the lesion confidences.

2. The method as claimed in claim 1, wherein the deep learning model is obtained by pre-training as follows:
    obtaining each medical image sample for training;
    for each medical image sample, marking a mark value corresponding to each preset lesion type, and obtaining a mark sequence corresponding to each medical image sample, wherein each element in the mark sequence is the mark value corresponding to each preset lesion type, and wherein in each medical image sample, a mark value corresponding to the preset lesion type that is positive is 1, and a mark value corresponding to the preset lesion type that is negative is 0;
    for each marked medical image sample, inputting each medical image sample into the deep learning model for iterative training, and obtaining a sample sequence corresponding to each medical image sample output from the deep learning model, wherein each element in the sample sequence is a second confidence corresponding to each preset lesion type, and wherein the second confidence represents a probability that each medical image sample belongs to a corresponding preset lesion type;
    adjusting model parameters of the deep learning model with a calculation result of a preset loss function as an adjustment target until the calculation result of the loss function converges and is less than a preset convergence threshold, wherein the loss function is used for calculating an error between the sample sequence and the mark sequence corresponding to each medical image sample; and
    after the calculation result of the loss function converges and is less than the preset convergence threshold, determining that the deep learning model has been trained.

3. The method as claimed in claim 2, further comprising before inputting each medical image sample into the deep learning model for iterative training to obtain the sample sequence corresponding to each medical image sample output from the deep learning model:
    randomly scrambling an order of inputting each marked medical image sample into the deep learning model.

4. The method as claimed in claim 1, wherein determining the maximum connected area in the generic activation map corresponding to each preset lesion type, and creating the mark border surrounding the maximum connected area comprises:
    for the generic activation map corresponding to each preset lesion type, obtaining a maximum pixel value of the point on the generic activation map;
    calculating the product of the maximum pixel value and a preset proportion value to obtain a boundary pixel threshold, wherein the preset proportion value is greater than 0 and less than 1;
    creating an initial border, and adjusting the initial border to minimize a bounding area of the initial border, wherein the initial border surrounds all points whose pixel value is greater than the boundary pixel threshold on the generic activation map;
    detecting the maximum connected area in the bounding area of the initial border; and
    creating a mark border, and adjusting the mark border to minimize a bounding area of the mark border, wherein the mark border surrounds the maximum connected area.

5. The method as claimed in claim 1, wherein for each preset lesion type, calculating the fusion feature map corresponding to each preset lesion type according to the first feature map and the weight value corresponding to each preset lesion type comprises:
    for each preset lesion type, putting the first feature map and the weight value corresponding to each preset lesion type into a preset weighted sum formula to calculate the fusion feature map corresponding to each preset lesion type;
    wherein the weighted sum formula is:

$$F_c = \sum_{k=1}^{K} w_k^c \cdot f_k,$$

wherein $F_c$ is a vector value of the fusion feature map, K is the number of first feature maps extracted, c is the number of the preset lesion type, $f_k$ represents the k-th first feature map extracted, and $w_k^c$ represents the weight of the c-th preset lesion type corresponding to the k-th input unit in the fully connected layer.

6. A computer equipment, comprising:
    a memory, a processor, and a computer readable instruction stored in the memory and capable of running on the processor, wherein the processor, when executing the computer readable instruction, implements:
    obtaining a target medical image of a lesion to be detected;
    inputting the target medical image into a pre-trained deep learning model to obtain a target sequence output from the deep learning model, wherein each element in the target sequence is a first confidence corresponding to each preset lesion type, wherein the first confidence represents a probability that the target medical image belongs to a corresponding preset lesion type, wherein the deep learning model is obtained by pre-training a medical image sample corresponding to each preset lesion type, and wherein each medical image sample is marked with a lesion type comprised in the target medical image;

after inputting the target medical image into the deep learning model, extracting a first feature map output from a last convolution layer in the deep learning model;

extracting a weight value of each network unit corresponding to each preset lesion type in a fully connected layer of the deep learning model;

for each preset lesion type, calculating a fusion feature map corresponding to each preset lesion type according to the first feature map and the weight value corresponding to each preset lesion type;

resampling the fusion feature map corresponding to each preset lesion type to a size of the target medical image to generate a generic activation map corresponding to each preset lesion type;

determining a maximum connected area in the generic activation map corresponding to each preset lesion type, and creating a mark border surrounding the maximum connected area, wherein the maximum connected area refers to a connected area into which a point whose pixel value exceeds a specified pixel threshold falls in the generic activation map; and adding a mark border corresponding to each preset lesion type to the target medical image as a location result of the lesion to be detected, wherein the processor, when executing the computer readable instruction, further implements after inputting the target medical image into the pre-trained deep learning model to obtain the target sequence output from the deep learning model:

obtaining a preset confidence threshold corresponding to each preset lesion type;

comparing each element in the target sequence with the corresponding preset confidence threshold to determine an element greater than or equal to the preset confidence threshold in the target sequence, denoting it as a target element; and determining a prediction result of the preset lesion type corresponding to each target element on the target medical image to be positive, and determining the prediction result of the preset lesion types corresponding other elements on the target medical image to be negative, wherein the other elements refer to the elements in the target sequence other than the target element; and the preset confidence threshold corresponding to each preset lesion type is predetermined as follows:

obtaining each medical image that is collected in advance for verification and denoting it as each verification sample;

for each verification sample, inputting each verification sample into the pre-trained deep learning model, and obtaining a verification sequence corresponding to each verification sample output from the deep learning model, wherein each element in the verification sequence is a third confidence corresponding to each preset lesion type, and wherein the third confidence represents a probability that each verification sample belongs to a corresponding preset lesion type;

for each preset lesion type, extracting the third confidence corresponding to each preset lesion type in the verification sequence corresponding to each verification sample to obtain each lesion confidence;

for each preset lesion type, according to each lesion confidence, calculating a Yoden index with each lesion confidence as a threshold to obtain an index result corresponding to each lesion confidence; and determining the lesion confidence corresponding to the maximum index result as the preset confidence threshold corresponding to each preset lesion type, wherein the maximum index result refers to the maximum of the index results corresponding to the lesion confidences.

7. The computer equipment as claimed in claim 6, wherein the deep learning model is obtained by pre-training as follows:

obtaining each medical image sample for training;

for each medical image sample, marking a mark value corresponding to each preset lesion type, and obtaining a mark sequence corresponding to each medical image sample, wherein each element in the mark sequence is the mark value corresponding to each preset lesion type, and wherein in each medical image sample, a mark value corresponding to the preset lesion type that is positive is 1, and a mark value corresponding to the preset lesion type that is negative is 0;

for each marked medical image sample, inputting each medical image sample into the deep learning model for iterative training, and obtaining a sample sequence corresponding to each medical image sample output from the deep learning model, wherein each element in the sample sequence is a second confidence corresponding to each preset lesion type, and wherein the second confidence represents a probability that each medical image sample belongs to a corresponding preset lesion type;

adjusting model parameters of the deep learning model with a calculation result of a preset loss function as an adjustment target until the calculation result of the loss function converges and is less than a preset convergence threshold, wherein the loss function is used for calculating an error between the sample sequence and the mark sequence corresponding to each medical image sample; and after the calculation result of the loss function converges and is less than the preset convergence threshold, determining that the deep learning model has been trained.

8. The computer equipment as claimed in claim 6, wherein determining the maximum connected area in the generic activation map corresponding to each preset lesion type, and creating the mark border surrounding the maximum connected area comprises:

for the generic activation map corresponding to each preset lesion type, obtaining a maximum pixel value of the point on the generic activation map;

calculating the product of the maximum pixel value and a preset proportion value to obtain a boundary pixel threshold, wherein the preset proportion value is greater than 0 and less than 1;

creating an initial border, and adjusting the initial border to minimize a bounding area of the initial border, wherein the initial border surrounds all points whose pixel value is greater than the boundary pixel threshold on the generic activation map;

detecting the maximum connected area in the bounding area of the initial border; and creating a mark border, and adjusting the mark border to minimize a bounding area of the mark border, wherein the mark border surrounds the maximum connected area.

9. The computer equipment as claimed in claim 6, wherein for each preset lesion type, calculating the fusion feature map corresponding to each preset lesion type according to the first feature map and the weight value corresponding to each preset lesion type comprises:
for each preset lesion type, putting the first feature map and the weight value corresponding to each preset lesion type into a preset weighted sum formula to calculate the fusion feature map corresponding to each preset lesion type;
wherein the weighted sum formula is:

$$F_c = \sum_{k=1}^{K} w_k^c \cdot f_k,$$

wherein $F_c$ is a vector value of the fusion feature map, K is the number of first feature maps extracted, c is the number of the preset lesion type, $f_k$ represents the k-th first feature map extracted, and $w_k^c$ represents the weight of the c-th preset lesion type corresponding to the k-th input unit in the fully connected layer.

10. A non-transitory computer readable storage medium that stores a computer readable instruction, wherein the computer readable instruction, when executed by one or more processors, enables the one or more processors to perform:
obtaining a target medical image of a lesion to be detected;
inputting the target medical image into a pre-trained deep learning model to obtain a target sequence output from the deep learning model, wherein each element in the target sequence is a first confidence corresponding to each preset lesion type, wherein the first confidence represents a probability that the target medical image belongs to a corresponding preset lesion type, wherein the deep learning model is obtained by pre-training a medical image sample corresponding to each preset lesion type, and wherein each medical image sample is marked with a lesion type comprised in the target medical image;
after inputting the target medical image into the deep learning model, extracting a first feature map output from a last convolution layer in the deep learning model;
extracting a weight value of each network unit corresponding to each preset lesion type in a fully connected layer of the deep learning model;
for each preset lesion type, calculating a fusion feature map corresponding to each preset lesion type according to the first feature map and the weight value corresponding to each preset lesion type;
resampling the fusion feature map corresponding to each preset lesion type to a size of the target medical image to generate a generic activation map corresponding to each preset lesion type;
determining a maximum connected area in the generic activation map corresponding to each preset lesion type, and creating a mark border surrounding the maximum connected area, wherein the maximum connected area refers to a connected area into which a point whose pixel value exceeds a specified pixel threshold falls in the generic activation map; and
adding a mark border corresponding to each preset lesion type to the target medical image as a location result of the lesion to be detected, wherein
the computer readable instruction, when executed by the one or more processors, enables the one or more processors to further perform:
after inputting the target medical image into the pre-trained deep learning model to obtain the target sequence output from the deep learning model:
obtaining a preset confidence threshold corresponding to each preset lesion type;
comparing each element in the target sequence with the corresponding preset confidence threshold to determine an element greater than or equal to the preset confidence threshold in the target sequence, and denoting it as a target element; and
determining a prediction result of the preset lesion type corresponding to each target element on the target medical image to be positive, and determining the prediction result of the preset lesion types corresponding other elements on the target medical image to be negative, wherein the other elements refer to the elements in the target sequence other than the target element; and
the preset confidence threshold corresponding to each preset lesion type is predetermined as follows:
obtaining each medical image that is collected in advance for verification and denoting it as each verification sample;
for each verification sample, inputting each verification sample into the pre-trained deep learning model, and obtaining a verification sequence corresponding to each verification sample output from the deep learning model, wherein each element in the verification sequence is a third confidence corresponding to each preset lesion type, and wherein the third confidence represents a probability that each verification sample belongs to a corresponding preset lesion type;
for each preset lesion type, extracting the third confidence corresponding to each preset lesion type in the verification sequence corresponding to each verification sample to obtain each lesion confidence;
for each preset lesion type, according to each lesion confidence, calculating a Yoden index with each lesion confidence as a threshold to obtain an index result corresponding to each lesion confidence; and
determining the lesion confidence corresponding to the maximum index result as the preset confidence threshold corresponding to each preset lesion type, wherein the maximum index result refers to the maximum of the index results corresponding to the lesion confidences.

11. The non-transitory computer readable storage medium as claimed in claim 10, wherein the deep learning model is obtained by pre-training as follows:
obtaining each medical image sample for training;
for each medical image sample, marking a mark value corresponding to each preset lesion type, and obtaining a mark sequence corresponding to each medical image sample, wherein each element in the mark sequence is the mark value corresponding to each preset lesion type, and wherein in each medical image sample, a mark value corresponding to the preset lesion type that is positive is 1, and a mark value corresponding to the preset lesion type that is negative is 0;

for each marked medical image sample, inputting each medical image sample into the deep learning model for iterative training, and obtaining a sample sequence corresponding to each medical image sample output from the deep learning model, wherein each element in the sample sequence is a second confidence corresponding to each preset lesion type, and wherein the second confidence represents a probability that each medical image sample belongs to a corresponding preset lesion type;

adjusting model parameters of the deep learning model with a calculation result of a preset loss function as an adjustment target until the calculation result of the loss function converges and is less than a preset convergence threshold, wherein the loss function is used for calculating an error between the sample sequence and the mark sequence corresponding to each medical image sample; and after the calculation result of the loss function converges and is less than the preset convergence threshold, determining that the deep learning model has been trained.

12. The non-transitory computer readable storage medium as claimed in claim 11, wherein the computer readable instruction, when executed by the one or more processors, enables the one or more processors to further perform:

randomly scrambling an order of inputting each marked medical image sample into the deep learning model, before inputting each medical image sample into the deep learning model for iterative training to obtain the sample sequence corresponding to each medical image sample output from the deep learning model.

13. The non-transitory computer readable storage medium as claimed in claim 10, wherein the computer readable instruction operable with the one or more processors to perform determining the maximum connected area in the generic activation map corresponding to each preset lesion type, and creating the mark border surrounding the maximum connected area is operable with the one or more processors to perform:

for the generic activation map corresponding to each preset lesion type, obtaining the maximum pixel value of the point on the generic activation map;

calculating the product of the maximum pixel value and a preset proportion value to obtain a boundary pixel threshold, wherein the preset proportion value is greater than 0 and less than 1;

creating an initial border, and adjusting the initial border to minimize a bounding area of the initial border, wherein the initial border surrounds all points whose pixel value is greater than the boundary pixel threshold on the generic activation map;

detecting the maximum connected area in the bounding area of the initial border; and creating a mark border, and adjusting the mark border to minimize a bounding area of the mark border, wherein the mark border surrounds the maximum connected area.

14. The non-transitory computer readable storage medium as claimed in claim 10, wherein the computer readable instruction, when executed by the one or more processors, enables the one or more processors to perform calculating, for each preset lesion type, the fusion feature map corresponding to each preset lesion type according to the first feature map and the weight value corresponding to each preset lesion type, which comprises:

for each preset lesion type, putting the first feature map and the weight value corresponding to each preset lesion type into a preset weighted sum formula to calculate the fusion feature map corresponding to each preset lesion type;

wherein the weighted sum formula is:

$$F_c = \sum_{k=1}^{K} w_k^c \cdot f_k,$$

wherein $F_c$ is a vector value of the fusion feature map, K is the number of first feature maps extracted, c is the number of the preset lesion type, $f_k$ represents the k-th first feature map extracted, and $w_k^c$ represents the weight of the c-th preset lesion type corresponding to the k-th input unit in the fully connected layer.

* * * * *